United States Patent [19]

Kim

[11] Patent Number: 4,643,677
[45] Date of Patent: Feb. 17, 1987

[54] DENTAL INSTRUMENT

[76] Inventor: Daniel S. Y. Kim, 411 NE. 87th Ave., Vancouver, Wash. 98664

[21] Appl. No.: 752,559

[22] Filed: Jul. 8, 1985

[51] Int. Cl.⁴ ............................................. A61C 3/08
[52] U.S. Cl. ..................................... 433/164; 433/142
[58] Field of Search ........................ 433/164, 161, 142

[56] References Cited

U.S. PATENT DOCUMENTS

| 532,721 | 1/1895 | Dennis | 433/164 |
| 1,369,582 | 2/1921 | Wagner | 433/142 |

FOREIGN PATENT DOCUMENTS 451785  8/1936  United Kingdom ................ 433/164

OTHER PUBLICATIONS

"Kent Dental", Publication, p. 102, Kent Dental Supply Co., Inc., 25 Commerce Drive, Aston, PA 19014.

Primary Examiner—Robert Peshock
Attorney, Agent, or Firm—Lee R. Schermerhorn

[57] ABSTRACT

An elongated straight handle portion has a cylindrical plugger element on each end thereof. Each plugger element has a 45° bend adjacent the end of the handle and a 90° bend adjacent the distal end of the plugger element. Protruding laterally from the apex of each 90° bend is a burnishing element. The burnishing element on one end of the handle is ball shaped and the burnishing element on the other end is cone-shaped.

1 Claim, 4 Drawing Figures

U.S. Patent     Feb. 17, 1987     4,643,677
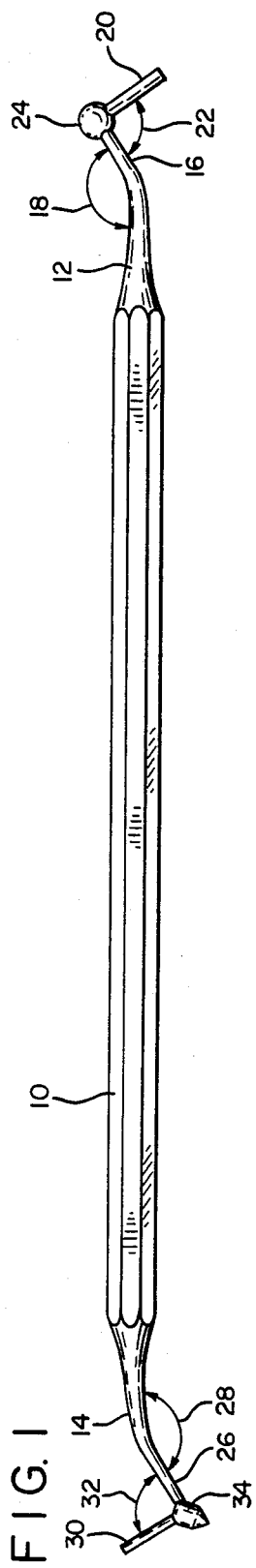
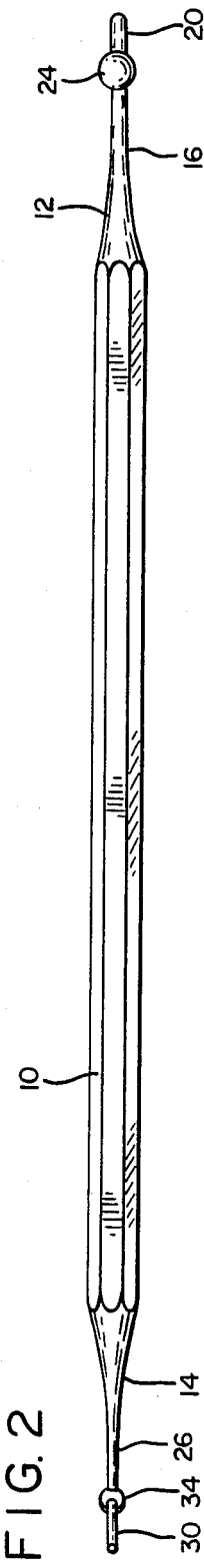
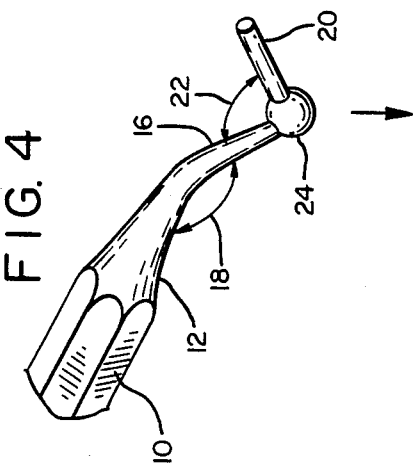
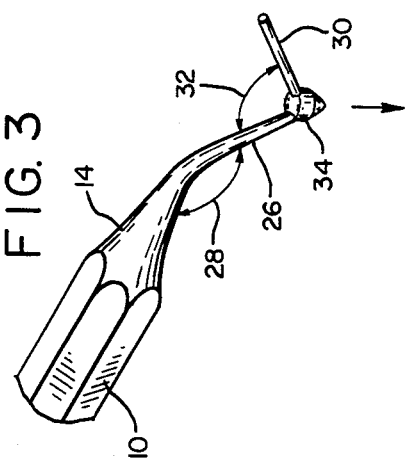

DENTAL INSTRUMENT

BACKGROUND OF THE INVENTION

This invention relates to a dental instrument for use by dentists in installing amalgam fillings in teeth.

Amalgam filling material for tooth cavities is formed as a pliable mixture of silver alloy and mercury. When the cavity preparation has been completed the titurated amalgam is carried by a carrier and placed in the cavity and packed therein by a cylindrical plugger. When the packed alloy reaches slightly above the carvo surface a ball shaped burnisher is used to spread and pack and roughly contour the amalgam filling and then a cone-shaped burnisher is used to form the anatomy of the filling briefly before carving by carver instruments.

During this procedure an assistant stands by to pass these various instruments to the dentist, paying close attention to which instruments the dentist wants to use. The assistant cannot do anything but await the dentist's request for one instrument after another. Both the assistant and the dentist are under stress because the assistant must respond correctly to the dentist's requests and the dentist is annoyed and delayed if the correct instrument is not passed at each request. Such mistakes interrupt the dentist's concentration on the work.

SUMMARY OF THE INVENTION

The present invention combines several of these instruments into a single instrument so that the assistant does not have to stand by for passing and retrieving instruments one by one. Instead, the assistant is free to do other work such as manipulating the amalgam and doing other things after the present single instrument has been passed to the dentist, thereby saving time in the tooth filling operation. The assistant is free of stress from thinking about the instruments, guessing which one the dentist will want next and waiting for the dentist's next request for an instrument.

At the same time the dentist does not have to pass several instruments back and forth and is not interrupted in his work on the patient. In summary, the present combined instrument minimizes the passing of instruments, saves time and relieves both dentists and assistants from a large part of the stress of tooth filling.

In the present instrument a burnisher is mounted on the plugger so that the same instrument is used for both plugging and burnishing. The burnisher may be a ball shape or it may be a cone shape. In the preferred embodiment, a large plugger on one end of the handle is equipped with a ball shaped burnisher and a small plugger on the opposite end of the handle is equipped with a cone-shaped burnisher whereby a single instrument takes the place of four separate instruments in conventional practice.

The invention will be better understood and the foregoing and additional features and advantages will become apparent from the following description of the preferred embodiment illustrated in the accompanying drawing. Various changes may be made in the details of construction and arrangement of parts and certain features may be used without others. All such modifications within the scope of the appended claims are included in the invention.

BRIEF DESCRIPTION OF THE DRAWINGS

FIG. 1 is a side elevation view of a dental instrument embodying the invention.

FIG. 2 is a top plan view of the instrument in FIG. 1.

FIG. 3 is an enlarged side elevation view of the left end portion of the instrument in FIGS. 1 and 2.

FIG. 4 is an enlarged side elevation view of the right end portion of the instrument in FIGS. 1 and 2.

DESCRIPTION OF THE PREFERRED EMBODIMENT

The present instrument has a straight elongated handle portion 10 with tapered end portions 12 and 14 at opposite ends thereof. On the right end of the instrument the proximal end of a cylindrical plugger element 16 extends from tapered portion 12 at a 45° angle at 18. The distal end 20 of the plugger makes a 90° angle at 22 with its proximal end. As seen in FIG. 2 these two angles at 18 and 22 are disposed in a common plane. A ball shaped burnishing element 24 protrudes outward from the apex of the 90° angle at 22.

On the opposite end of the instrument, a cylindrical plugger element 26 has a proximal end disposed at an angle of 45° at 28, with respect to the longitudinal axis of handle portion 10. Plugger element 26 is of slightly smaller diameter than plugger element 16. Distal end 30 is disposed at an angle of 90° at 32 with respect to the proximal end portion, both angles 28 and 32 being disposed in a common plane. As seen in FIG. 2, this is also the plane of angles 18 and 22 described above.

Projecting outward from the apex of the 90° angle at 32 is a cone-shaped burnisher 34. In use, the burnishers 24 and 34 are applied to the amalgam filling in the tooth in the direction of the arrows in FIGS. 3 and 4.

Thus the present instrument provides a combination of four different instruments on a single handle, whereby the dentist does not have to request these instruments individually from his assistant and the assistant does not have to stand by to hold the different instruments available one at a time on demand from the dentist. Plugger 16 provides a large plugger and plugger 26 provides a small plugger. Burnisher 24 provides a ball shaped burnisher and burnisher 34 provides a cone-shaped burnisher, all continuously in the dentist's hand while he is concentrating on the work to be done on the amalgam filling.

What is claimed is:

1. A dental instrument comprising a straight handle having a plugger on each opposite end thereof, each of said pluggers comprising a cylindrical extension on the handle having a proximal portion bent at approximately 45° to the axis of the handle and a distal portion bent at approximately 90° to said proximal portion and extending away from the adjacent end of the handle, a ball-shaped burnisher projecting outwardly from the apex of said 90° angle in one of said extensions, and a cone-shaped burnisher projecting outwardly from the apex of the 90° angle in the other extension.

* * * * *